United States Patent
Park et al.

(10) Patent No.: US 10,632,161 B1
(45) Date of Patent: Apr. 28, 2020

(54) METHOD FOR AMELIORATING OR TREATING A BOWEL DISEASE

(71) Applicant: PROSTEMICS CO. LTD., Seoul (KR)

(72) Inventors: Eun-Joo Park, Seoul (KR); Min-Koo Seo, Seoul (KR); Seong-Yeol Ko, Dongducheon-si (KR); Eun-Wook Choi, Seoul (KR); Won-Jong Lee, Seoul (KR)

(73) Assignee: PROSTEMICS CO. LTD., Seoul (KR)

( * ) Notice: Subject to any disclaimer, the term of this patent is extended or adjusted under 35 U.S.C. 154(b) by 0 days.

(21) Appl. No.: 16/420,792

(22) Filed: May 23, 2019

(51) Int. Cl.
  *A61K 35/747* (2015.01)
  *A61P 1/04* (2006.01)
  *C12N 1/02* (2006.01)
  *A23L 33/135* (2016.01)
  *C12N 1/20* (2006.01)

(52) U.S. Cl.
  CPC .......... *A61K 35/747* (2013.01); *A23L 33/135* (2016.08); *A61P 1/04* (2018.01); *C12N 1/02* (2013.01); *C12N 1/20* (2013.01); *A23V 2002/00* (2013.01); *A23V 2200/32* (2013.01); *A23Y 2220/47* (2013.01)

(58) Field of Classification Search
  CPC .... A61K 35/747; C12N 1/02; A23V 2200/32; A23Y 2220/47
  See application file for complete search history.

(56) References Cited

U.S. PATENT DOCUMENTS

2014/0193383 A1  7/2014  Lemieux et al.

FOREIGN PATENT DOCUMENTS

| KR | 10-2018-0059299 A | 6/2018 |
| KR | 10-2018-0072589 A | 6/2018 |
| WO | 2006/084381 A1 | 8/2006 |
| WO | WO 2012093755 | * 7/2012 |

OTHER PUBLICATIONS

Maeda et al., Bioscience Microflora, 2003, vol. 22, No. 2, p. 45-50.*
Li et al., BMC Microbiology, 2017, vol. 17, No. 66, p. 1-8.*
Berlec et al., "In vivo imaging of Lactococcus lactis, Lactobacillus plantarum and *Escherichia coli* expressing infrared fluorescent protein in mice", Microb Cell Fact, 2015, vol. 14, p. 181 (14 pages).
Van Zyl et al., "In vivo bioluminescence imaging of the spatial and temporal colonization of lactobacillus plantarum 423 and enterococcus mundtii ST4SA in the intestinal tract of mice", BMC Microbiology, 2018, vol. 18, p. 171 (16 pages).

* cited by examiner

*Primary Examiner* — Kade Ariani
(74) *Attorney, Agent, or Firm* — Vorys, Sater, Seymour & Pease LLP; Mih Suhn Koh

(57) ABSTRACT

The present invention provides a method for ameliorating or treating inflammatory bowel disease (IBD) and/or irritable bowel syndrome (IBS), comprising administering extracellular vesicles derived from Kefir grains in a mammal in need thereof. The present invention also provides a pharmaceutical composition for ameliorating or treating IBD and/or IBS or a functional food composition for ameliorating or improving IBD and/or IBS, comprising said extracellular vesicles derived from Kefir grains as an active ingredient.

7 Claims, 14 Drawing Sheets

METHOD FOR AMELIORATING OR TREATING A BOWEL DISEASE

TECHNICAL FIELD

The present invention relates to a method for ameliorating or treating a bowel disease. More specifically, the present invention relates to a method for ameliorating or treating inflammatory bowel disease (IBD) and/or irritable bowel syndrome (IBS), comprising administering extracellular vesicles derived from Kefir grains to a mammal in need thereof.

BACKGROUND ART

Inflammatory bowel disease (IBD) is a group of inflammatory conditions of the colon and small intestine. Crohn's disease and colitis (e.g., ulcerative colitis) are the principal types of IBD. Ulcerative colitis causes long-lasting inflammation and ulcers in the innermost lining of the colon and the rectum. Crohn's disease is characterized by inflammation of the lining of the gastrointestinal tract, which often spreads deep into affected tissues. Both ulcerative colitis and Crohn's disease usually involve severe diarrhea, abdominal pain, fatigue and weight loss. IBD is a complex disease which arises as a result of the interaction of environmental and genetic factors leading to immunological responses and inflammation in the intestine.

Irritable bowel syndrome (IBS) is a common disorder that affects the large intestine. Signs and symptoms include cramping, abdominal pain, bloating, gas, and diarrhea or constipation, or both. IBS impairs the social and personal life of patients and thus negatively affects quality of life. Although the various causes, such as stress, sensitive personality, irregular eating habits, chronic fatigue, irritating and oily food, and so on, have been suggested, the causes of IBS have not yet been elucidated clearly. The currently-available methods could not provide effective therapy and the satisfactory treating method thereof is not yet known. Therefore, the IBS patients rely only on the improvement of symptoms. It has been reported that the number of patients suffered from IBS increased to about 1.62 million in 2012, an increase of approximately 8.7% (13 millions) over the past five years, with an average annual increase of 1.7%. Most patients (about 99.4% of the total patients) visit the clinic and receive only therapy for the relief of symptoms.

WO 2006/084381 has disclosed a probiotic composition comprising novel microorganisms belong to *Lactobacillus kefiranofaciens* and a method for providing modulation of the intestinal microflora in a subject comprising administering to said subject the novel microorganisms belong to *Lactobacillus kefiranofaciens*. However, it has been reported that, when *Lactobacillus* microorganisms are orally administered, the number of the microorganisms in the intestinal tract is rapidly reduced in a few hours (Berlec et al., In vivo imaging of *Lactococcus lactis, Lactobacillus plantarum* and *Escherichia coli* expressing infrared fluorescent protein in mice, Microb Cell Fact (2015) 14:181, DOI 10.1186/s12934-015-0376-4; Van Zyl et al., In vivo bioluminescence imaging of the spatial and temporal colonization of *Lactobacillus plantarum* 423 and *enterococcus* mundtii ST4SA in the intestinal tract of mice, BMC Microbiology (2018) 18:171, doi.org/10.1186/s12866-018-1315-4). Therefore, it is unsatisfactory to ameliorate or treat a bowel disease, through probiotic effects by using microorganisms per se.

Therefore, there is a need in the art to develop a new material for ameliorating or treating a bowel disease including IBD and/or IBS, in addition to providing relief of symptoms thereof.

DISCLOSURE

Technical Problem

The present inventors carried out various researches in order to develop a new material for ameliorating or treating a bowel disease including IBD and/or IBS. As the results thereof, the present inventors have found that the extracellular vesicles derived from Kefir grains exhibit not only excellent anti-inflammatory effects but also excellent effects for improving IBD (e.g. ulcerative colitis) and IBS.

Therefore, It is an object of the present invention to provide a method for ameliorating or treating IBD and/or IBS, comprising administering said extracellular vesicles derived from Kefir grains to a mammal in need thereof.

It is another object of the present invention to provide a pharmaceutical composition for ameliorating or treating IBD and/or IBS, comprising said extracellular vesicles derived from Kefir grains as an active ingredient.

It is still another object of the present invention to provide a functional food composition for ameliorating or improving IBD and/or IBS, comprising said extracellular vesicles derived from Kefir grains as an active ingredient.

Technical Solution

In accordance with an aspect of the present invention, there is provided a method for ameliorating or treating inflammatory bowel disease and/or irritable bowel syndrome in a mammal in need thereof, comprising administering to the mammal a therapeutically effective amount of extracellular vesicles derived from Kefir grains.

In the method of the present invention, the Kefir grains may be one or more selected from the group consisting of *Lactobacillus kefiranofaciens, Lactobacillus kefiri*, and *Lactobacillus kefirgranum*. In an embodiment, the inflammatory bowel disease may be Crohn's disease or colitis (including ulcerative colitis). The extracellular vesicles may be in the form of exosomes having a diameter ranging from 30 to 300 nm and have a mean diameter ranging from 120 to 190 nm.

The extracellular vesicles may be prepared by a process comprising (a) culturing one or more Kefir grains in a medium; (b) performing a centrifugation of the culture obtained in Step (a) to obtain a supernatant, thereby removing the Kefir grains; and (c) performing an ultracentrifugation of the supernatant obtained in Step (b) to obtain the resulting extracellular vesicles in the form of pellets.

In an embodiment, the centrifugation of Step (b) may be carried out under a rotation speed ranging from 5,000 g to 20,000 g and at a temperature below 20° C. In another embodiment, the centrifugation of Step (b) may be also carried out by (i) a first centrifugation of the culture obtained in Step (a) under a rotation speed ranging from 100 g to 1,000 g and at a temperature below 20° C. to obtain a supernatant; (ii) a second centrifugation of the supernatant obtained in Step (i) under a rotation speed ranging from 1,000 g to 5,000 g and at a temperature below 20° C. to obtain a supernatant; and then (iii) a third centrifugation of the supernatant obtained in Step (ii) under a rotation speed ranging from 5,000 g to 20,000 g and at a temperature below 20° C. In still another embodiment, the ultracentrifugation of Step (c) may be carried out under a rotation speed ranging from 100,000 g to 150,000 g and at a temperature below 20° C.

Advantageous Effects

It has been found by the present invention that the extracellular vesicles derived from Kefir grains exhibit not only excellent anti-inflammatory effects but also excellent effects for improving IBD (e.g. ulcerative colitis) and IBS. Especially, the extracellular vesicles derived from Kefir grains exhibit excellent effects for inhibiting the expression and/or secretion of proinflammatory cytokines; for improving bowel activity; and for inhibiting the proliferation of harmful enteric bacteria, thereby inducing the death thereof. Therefore, the method of the present invention can be effectively applied to ameliorating or treating a bowel disease including IBD and/or IBS. And also, the composition of the present invention can be used in a wide range of applications for ameliorating, improving or treating a bowel disease including IBD and/or IBS.

DESCRIPTION OF DRAWINGS

In FIG. 6, 'CONT' means the control group and 'EV' means the group treated with the extracellular vesicles.

In FIG. 7, 'CONT' means the control group and 'EV' means the group treated with the extracellular vesicles.

In FIG. 8, 'CONT' means the control group and 'EV' means the group treated with the extracellular vesicles.

In FIG. 9, 'CONT' means the control group and 'EV' means the group treated with the extracellular vesicles.

In FIG. 10, G1 is the normal control group, G2 is the colitis-induced control group, G3 is the positive control group, G4 is the group in which the extracellular vesicles were administered at a dose of 10 μg/mouse, and G5 is the group in which the extracellular vesicles were administered at a dose of 1 mg/mouse.

In FIG. 11, G1 is the normal control group, G2 is the colitis-induced control group, G3 is the positive control group, G4 is the group in which the extracellular vesicles were administered at a dose of 10 μg/mouse, and G5 is the group in which the extracellular vesicles were administered at a dose of 1 mg/mouse.

In FIG. 16, G1 is the normal control group, G2 is the colitis-induced control group, G3 is the positive control group, G4 is the group in which the extracellular vesicles were administered at a dose of 10 μg/mouse, and G5 is the group in which the extracellular vesicles were administered at a dose of 1 mg/mouse.

In FIG. 17, A1 is the normal control group; A2 is the IBD-induced control group in which physiological saline was orally administered; A3 is the positive control group which prednisolone was orally administered in the dose of 2 mg/kg; A4 is the group in which the mixed microorganisms ($5 \times 10^7$ CFU) were orally administered; A5 is the group in which the extracellular vesicles were orally administered at a dose of 10 μg/mouse; A6 is the group in which the commercially available *Lactobacillus* strains (5×10$^7$ CFU) were orally administered; and A7 is the group in which the extracellular vesicles (10 μg/mouse) and the commercially available *Lactobacillus* strains (5×10$^7$ CFU) were orally administered.

BEST MODE

Figure 1A:
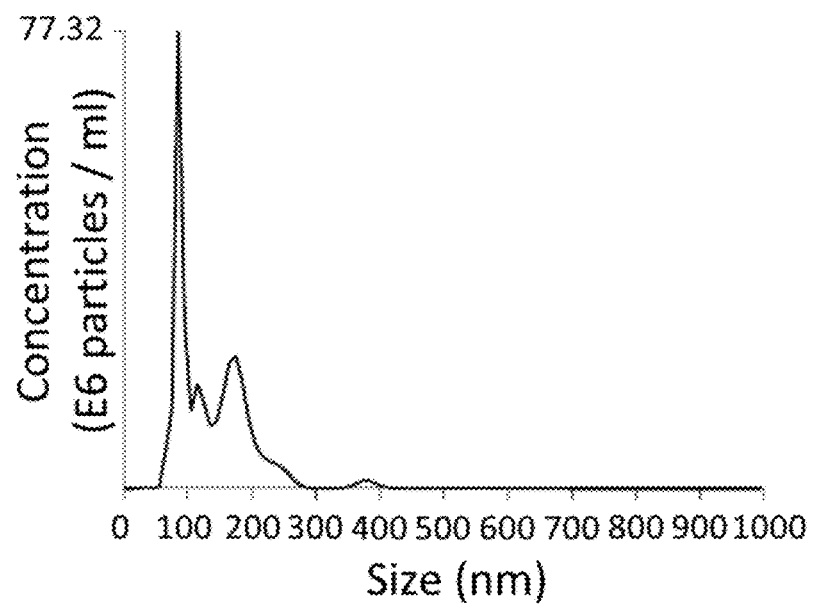
FIG. 1a shows the results by measuring the size distribution of the *Lactobacillus kefiri*-derived extracellular vesicles obtained in Example 1 with a nanoparticle tracking analyzer.

The present invention provides a method for ameliorating or treating inflammatory bowel disease and/or irritable bowel syndrome in a mammal in need thereof, comprising administering to the mammal a therapeutically effective amount of extracellular vesicles derived from Kefir grains.

As used herein, the term "Kefir" refers to a kind of fermented milk derived from the mountains of the Caucasus, which Tibetan monks drink popularly for health. Kefir includes proteins, polysaccharides, and other nutrients such as vitamin A, vitamin B1, vitamin B2, vitamin B6, vitamin D, vitamin K2, folic acid, nicotinic acid or its calcium salt, iron and iodine. The Kefir is usually in the form of a fermented milk drink similar to yoghurt, which is obtained by fermenting milk with Kefir grains (also referred to as Kefir granule strain) belonging to *Lactobacillus* strains as an initiator.

As used herein, the term "Kefir grains" refers to one or more *Lactobacillus* strains which are able to produce extracellular vesicles having activities for ameliorating or improving IBD and/or IBS as well as for providing inhibition against inflammation. Preferably, the Kefir grains may be one or more selected from the group consisting of *Lactobacillus kefiranofaciens, Lactobacillus kefiri*, and *Lactobacillus kefirgranum*. More preferably, the Kefir grains may be *Lactobacillus kefiranofaciens*.

As used herein, the term "extracellular vesicles" refers to small vesicles of membrane structure that are released from various cells. Therefore, the term "extracellular vesicles derived from Kefir grains" refers to small vesicles of membrane structure that are released from Kefir grains. The extracellular vesicles are also called as nanovesicles. The diameter of extracellular vesicles ranges, e.g., from approximately 30 to 1,000 nm. The method of the present invention comprises administering said extracellular vesicles derived from Kefir grains in an isolated form (i.e., not in the form of Kefir grains per se) as an active ingredient. Therefore, since the method of the present invention does not comprise administering *Lactobacillus* microorganisms per se, the method of the present invention can solve the problems associated with the conventional methods according to probiotic effects. In an embodiment of the present invention, the extracellular vesicles may be in the form of exosomes, which are intracellularly released from an endosome (multivesicular body) being fused with the plasma membrane. In an embodiment of the present invention, the extracellular vesicles may be in the form of exosomes having a diameter ranging from 30 to 300 nm. Preferably, the exosomes may have a mean diameter ranging from 120 to 190 nm.

In the method of the present invention, the inflammatory bowel disease may be Crohn's disease or colitis (including ulcerative colitis). And also, the irritable bowel syndrome may be diarrhea-predominant IBS (i.e., IBS-D), constipation-predominant IBS (i.e., IBS-C), and/or mixed-type IBS of IBS-D and IBSC (i.e., IBS-M).

In the method of the present invention, the Kefir grains-derived extracellular vesicles may be obtained by various processes, for example an ultracentrifugation method, an Exoquick method using commercially available ExoQuick™ Exosome Precipitation Solution, or a precipitation method. Preferably, the Kefir grains-derived extracellular vesicles may be obtained by an ultracentrifugation method.

In an embodiment of the present invention, the Kefir grains-derived extracellular vesicles may be obtained by an ultracentrifugation method. Specifically, the Kefir grains-derived extracellular vesicles may be prepared by a process comprising (a) culturing one or more Kefir grains in a medium; (b) performing a centrifugation of the culture obtained in Step (a) to obtain a supernatant, thereby removing the Kefir grains; and (c) performing an ultracentrifugation of the supernatant obtained in Step (b) to obtain the resulting extracellular vesicles in the form of pellets.

Before the culturing of Step (a), if necessary, a seed culturing may be carried out. For example, the seed culturing may be carried out in a solid medium (e.g., Lactobacilli MRS Agar) for 12 to 48 hours, followed by carrying out suspension culture in a liquid medium (e.g., Lactobacilli MRS Broth) for 1 to 48 hours. The culturing of Step (a), i.e., suspension culture of the harvested Kefir grains, may be carried out in an appropriate medium for about 1 to 14 days, preferably for about 1 to 7 days, more preferably for about 3 to 5 days, most preferably for about 4 days. The medium for the culturing of Step (a) includes a MRS medium (e.g., Lactobacilli MRS Broth) or dairy products such as milk and cheese, but not limited thereto. In an embodiment, the culturing of Step (a) may be carried out under the condition of optical density (OD) ranging from 2 to 2.5 by controlling the culturing time and/or the inoculation amounts, thereby maximizing the numbers of extracellular vesicles derived from Kefir grains.

Step (b) is a centrifugation step for removing the microorganisms, i.e., Kefir grains, from the culture. In an embodiment, Step (b) may be carried out under a rotation speed ranging from 5,000 g to 20,000 g and at a temperature below 20° C. In another embodiment, Step (b) may be carried out through multi-step centrifugations. For example, the centrifugation of Step (b) may be carried out by (i) a first centrifugation of the culture obtained in Step (a) under a rotation speed ranging from 100 g to 1,000 g and at a temperature below 20° C. to obtain a supernatant; (ii) a second centrifugation of the supernatant obtained in Step (i) under a rotation speed ranging from 1,000 g to 5,000 g and at a temperature below 20° C. to obtain a supernatant; and then (iii) a third centrifugation of the supernatant obtained in Step (ii) under a rotation speed ranging from 5,000 g to 20,000 g and at a temperature below 20° C. The first centrifugation may be carried out for 5 minutes to 1 hour, preferably for about 10 minutes, but not limited thereto. The second centrifugation may be carried out for 10 minutes to 1 hour, preferably for about 20 minutes, but not limited thereto. The third centrifugations may be carried out for 10 minutes to 1 hour, preferably for about 20 minutes, but not limited thereto.

The ultracentrifugation of Step (c) may be carried out under a rotation speed ranging from 100,000 g to 150,000 g and at a temperature below 20° C. The ultracentrifugation of Step (c) may be carried out for 1 to 3 hours, preferably for about 1 hour and 10 minutes, but not limited thereto. The resulting extracellular vesicles are obtained in the form of pellets, which may be suspended in an appropriate biocompatible medium (e.g., phosphate buffered saline) for storage thereof.

In another embodiment of the present invention, the Kefir grains-derived extracellular vesicles may be obtained by an Exoquick method using commercially available ExoQuick™ Exosome Precipitation Solution, according to the manufacturers protocol.

In still another embodiment of the present invention, the Kefir grains-derived extracellular vesicles may be obtained by a precipitation method. Specifically, the Kefir grains-derived extracellular vesicles may be prepared by a process comprising (a) culturing one or more Kefir grains in a medium; (b') performing a centrifugation of the culture obtained in Step (a) under a rotation speed ranging from 3,000 g to 5,000 g for 5 minutes to 1 hour, preferably for about 10 minutes, and at a temperature below 20° C. to obtain a supernatant; (c') adding to the supernatant 0.5 to 2N sodium acetate in a ratio of 0.1 to 1.5 ml, preferably 0.1 to 1 ml, per 10 ml of the supernatant, followed by incubating at a temperature ranging from −10° C. to 0° C. for 30 to 60 minutes, preferably for about 45 minutes; (d') performing a centrifugation of the supernatant obtained in Step (c') under a rotation speed ranging from 3,000 g to 5,000 g for 5 minutes to 1 hour, preferably for about 10 minutes, and at a temperature below 20° C. to obtain the resulting precipitate in the form of pellets. If necessary, in order to increase the purity thereof, the resulting precipitate may be additionally washed with 0.05 to 0.2N sodium acetate and then centrifuged under a rotation speed ranging from 3,000 g to 5,000 g for 5 minutes to 1 hour, preferably for about 10 minutes, and at a temperature below 20° C. to obtain the resulting precipitate in the form of pellets.

In the method of the present invention, the therapeutically effective amount of the Kefir grains-derived extracellular vesicles can be appropriately determined by a person having ordinary skill in the art. For example, the Kefir grains-derived extracellular vesicles may orally administered in an amount ranging from $1\times10^3$ to $1\times10^9$ particles, per day, but not limited thereto. The administration may be completed once or through several times per day.

The present invention includes, within its scope, a pharmaceutical composition for ameliorating or treating IBD and/or IBS, comprising a therapeutically effective amount of extracellular vesicles derived from Kefir grains as an active ingredient. The Kefir grains may be one or more selected from the group consisting of *Lactobacillus kefiranofaciens, Lactobacillus kefiri*, and *Lactobacillus kefirgranum*.

The pharmaceutical composition of the present invention may be formulated to various dosage forms such as capsules, tablets, powders, granules, injections, solutions, suspensions, emulsions, etc. For example, the pharmaceutical composition of the present invention may be formulated to an oral dosage form such as powders, granules, tablets, capsules, troches, elixir, solution, suspensions, emulsions, syrups, wafers, sustained-release preparations and the like; or to a parenteral dosage form such as injections (including in the form of sing-dosing ampoule or multiple-dosing ampoules), suppositories, and the like, according to conventional methods. The pharmaceutical composition of the present invention may further comprise one or more pharmaceutically acceptable carriers. The pharmaceutically acceptable carriers include a binder, a lubricant, a disintegrating agent, a diluent, a solubilizing agent, a dispersing agent, a stabilizing agent, a suspending agent, a pigment, a flavoring agent and the like in case of an oral dosage form; and a buffering agent, a preservative, a pain-relieving agent, a solubilizing agent, an isotonic agent, a stabilizing agent and the like in case of a parenteral dosage form. In the case of a topical dosage form, a base, an excipient, a lubricant, a preservative and the like may be used. Said dosage forms may be prepared according to conventional methods, using the pharmaceutically acceptable carriers as described above. And also, the dosage forms may be various forms, e.g., a dosage form for single administration or for multiple administrations.

Examples of carriers, additives and diluents include, but not limited to, lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil and the like. And also, a filler, an anticoagulant, a lubricant, a wetting agent, a flavoring agent, an emulsifying agent, a preservative and the like may be also included.

The pharmaceutical composition of the present invention may be administered orally or parenterally, including intravenous, intramuscular, subcutaneous, rectal and topical routes of administration. Preferably, the pharmaceutical composition of the present invention may be administered orally or rectally (e.g., in the form or suppository).

In the pharmaceutical composition of the present invention, a dose of the Kefir grains-derived extracellular vesicles may vary depending on patient's state or body weight, seriousness of disease, dosage forms, administration routes, and the period of administration, and can be appropriately determined by a person having ordinary skill in the art. For example, the Kefir grains-derived extracellular vesicles can be administered in an amount ranging from $1\times10^3$ to $1\times10^9$ particles, per day to a subject, but not limited thereto. The administration can be completed once or through several times per day. In the pharmaceutical composition of the present invention, the Kefir grains-derived extracellular vesicles may be present in the range of 0.1 to 50% by weight based on 100% by weight of the pharmaceutical composition.

And also, the present invention, within its scope, a food composition for ameliorating or improving IBD and/or IBS, comprising the extracellular vesicles derived from Kefir grains as an active ingredient. The food composition according to the present invention can be used as a health functional food. The Kefir grains may be one or more selected from the group consisting of *Lactobacillus kefiranofaciens, Lactobacillus kefiri*, and *Lactobacillus kefirgranum*.

The food composition of the present invention may be prepared in various forms, e.g., beverages, gums, teas, vitamin complexes, powders, granules, tablets, capsules, snacks, rice cakes, breads and the like. In the food composition of the present invention, the Kefir grains-derived extracellular vesicles may be present in the range of 0.1 to 50% by weight based on 100% by weight of the food composition.

The food composition of the present invention may include various additional ingredients, such as sweeteners/flavors or natural carbohydrates. Examples of the natural carbohydrates include conventional sugars such as monosaccharides (e.g., glucose), disaccharides (e.g., fructose), polysaccharides (e.g., sucrose), dextrin and cyclodextrin; and sugar alcohols such as xylitol, sorbitol and erythritol. Examples of the sweeteners/flavors include natural flavors (e.g., thaumatin, stevia leaf extract (for example, rebaudioside A, and glycyrrhizin)), and synthetic flavors (e.g., saccharine and aspartame). In addition, the food composition of the present invention may include various nutrients, vitamins, minerals (electrolytes), flavors such as synthetic flavors and natural flavors, colorants, pectic acid or a salt thereof, alginic acid or a salt thereof, stabilizers, preservatives, glycerin, alcohols, carbonating agents used in carbonated beverages, and the like. These ingredients may be used independently or in combination and may be present in the range of 0.1 to 50% by weight based on 100% by weight of the food composition, but not limited thereto.

The present invention will be described in further detail with reference to the following examples and experimental examples. These examples and experimental examples are for illustrative purposes only and are not intended to limit the scope of the present invention.

Example 1: Preparations of the Kefir Grains-Derived Extracellular Vesicles and Characterizations Thereof

*Lactobacillus kefiranofaciens* (KCTC 5075, Korean Collection for Type Cultures) was streaked on the Lactobacilli MRS Agar (BD, USA, 288120) and then cultured at 37° C. for 24 hours. The harvested *Lactobacillus kefiranofaciens* was subject to the suspension culture in the Lactobacilli MRS Broth (BD, USA, 288130) for 24 hours in a small scale (i.e., in the 50 ml scale). And then, the harvested *Lactobacillus* kefiranofaciens was subject to the suspension culture in the Lactobacilli MRS Broth (BD, USA, 288130) in a large scale (i.e., in the 1000 ml scale) under controlling the OD value to about 2 to 2.5. On the fourth day of the suspension culture, the culture was centrifuged under the rotation speed of 300 g at 4° C. for 10 minutes. The resulting supernatant was centrifuged under the rotation speed of 1,200 g at 4° C. for 20 minutes. The resulting supernatant was centrifuged under the rotation speed of 10,000 g at 4° C. for 30 minutes. The resulting supernatant was ultra-centrifuged under the rotation speed of 110,000 g at 4° C. for 1 hour and 10 minutes to discard the resulting supernatant, thereby obtaining pellets.

*Lactobacillus kefiri* (KTCT 3611, Korean Collection for Type Cultures) and *Lactobacillus kefirgranum* (KTCT 5086, Korean Collection for Type Cultures) were also cultured in the same procedures as in *Lactobacillus kefiranofaciens*. In addition, the *Lactobacillus kefiri*-derived pellets and *Lactobacillus kefirgranum*-derived pellets were also obtained in same procedures as in *Lactobacillus kefiranofaciens*-derived pellets.

The obtained pellets were respectively suspended in phosphate buffered saline (1 ml) and then the numbers and the mean diameters of the extracellular vesicles, which were respectively derived from *Lactobacillus kefiranofaciens*, *Lactobacillus kefiri* and *Lactobacillus kefirgranum*, were measured, using a nanoparticle tracking analyzer (Nanosight NS300). The results thereof are shown in FIGS. 1a to 1c and the following table 1.

TABLE 1

| Microorganism | Number of particles/ml |
|---|---|
| *Lactobacillus kefiranofaciens* | $6.0 \times 10^{11}$ |
| *Lactobacillus kefiri* | $3.0 \times 10^{11}$ |
| *Lactobacillus kefirgranum* | $3.0 \times 10^{11}$ |

Figure 1B:
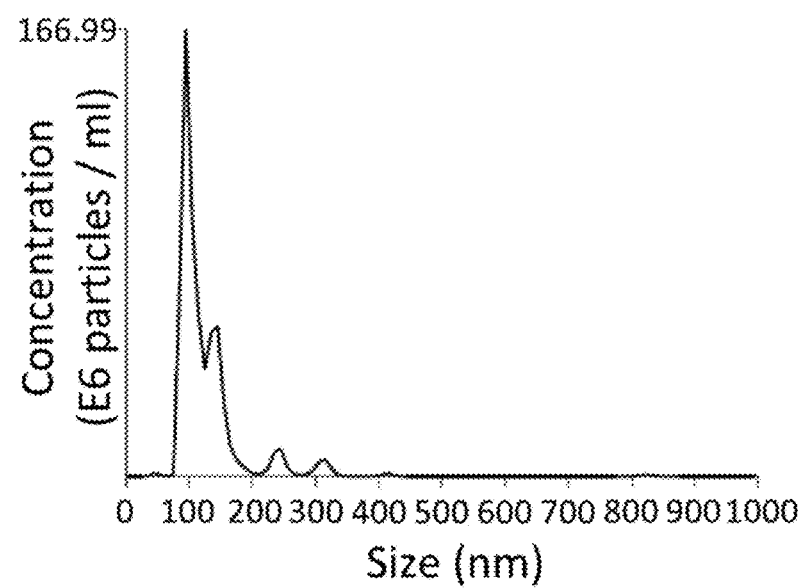
FIG. 1b shows the results by measuring the size distribution of the *Lactobacillus kefiranofaciens*-derived extracellular vesicles obtained in Example 1 with a nanoparticle tracking analyzer.
Figure 1C:
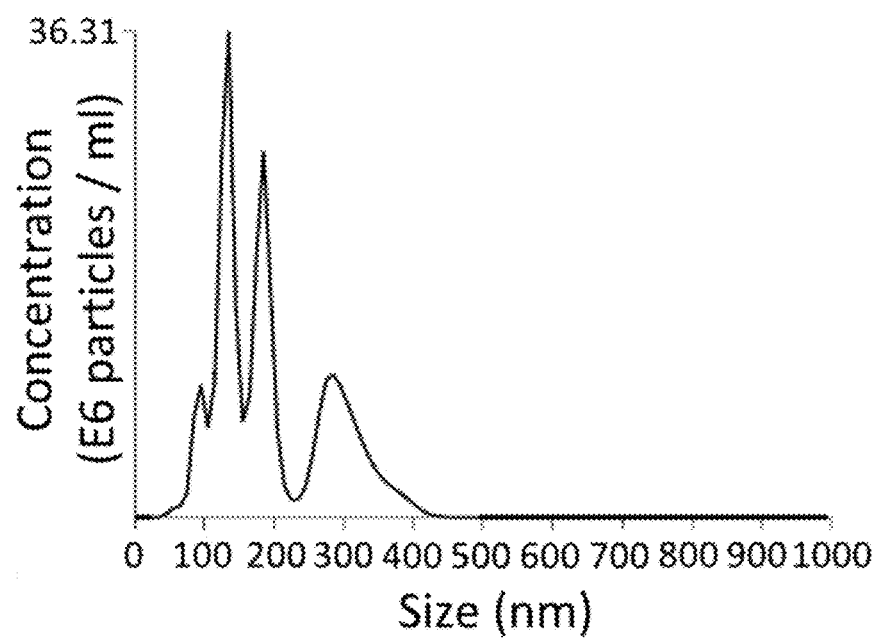
FIG. 1c shows the results by measuring the size distribution of the *Lactobacillus kefirgranum*-derived extracellular vesicles obtained in Example 1 with a nanoparticle tracking analyzer.

As shown in FIGS. 1a to 1c and the table 1, the extracellular vesicles were present in an amount of $4.5 \times 10^{11}$ particles per 1 ml and the mean diameter thereof was 120 to 190 nm.

Example 2: Yields of the Kefir Grains-Derived Extracellular Vesicles According to the Culturing Times

*Lactobacillus kefiranofaciens* (KCTC 5075, Korean Collection for Type Cultures) was streaked on the Lactobacilli MRS Agar (BD, USA, 288120) and then cultured at 37° C. for 24 hours. The harvested *Lactobacillus kefiranofaciens* was subject to the suspension culture in the Lactobacilli MRS Broth (BD, USA, 288130) for 24 hours in a small scale (i.e., in the 50 ml scale). And then, the harvested *Lactobacillus* kefiranofaciens was subject to the suspension culture in the Lactobacilli MRS Broth (BD, USA, 288130) in a large scale (i.e., in the 1000 ml scale) under controlling the OD value to about 2 to 2.5. On the first, second, third, fourth and seventh days of the suspension culture, the resulting cultures was respectively centrifuged under the rotation speed of 300 g at 4° C. for 10 minutes. The resulting supernatants were respectively centrifuged under the rotation speed of 1,200 g at 4° C. for 20 minutes. The resulting supernatants were respectively centrifuged under the rotation speed of 10,000 g at 4° C. for 30 minutes. The resulting supernatants were respectively ultra-centrifuged under the rotation speed of 110,000 g at 4° C. for 1 hour and 10 minutes to discard the resulting supernatants, thereby obtaining the respective pellets.

*Lactobacillus kefiri* (KCTC 3611, Korean Collection for Type Cultures) and *Lactobacillus kefirgranum* (KTCT 5086, Korean Collection for Type Cultures) were also cultured in the same procedures as in *Lactobacillus kefiranofaciens*. In addition, the *Lactobacillus kefiri*-derived pellets and *Lactobacillus kefirgranum*-derived pellets were also obtained in same procedures as in *Lactobacillus kefiranofaciens*-derived pellets.

Figure 2:
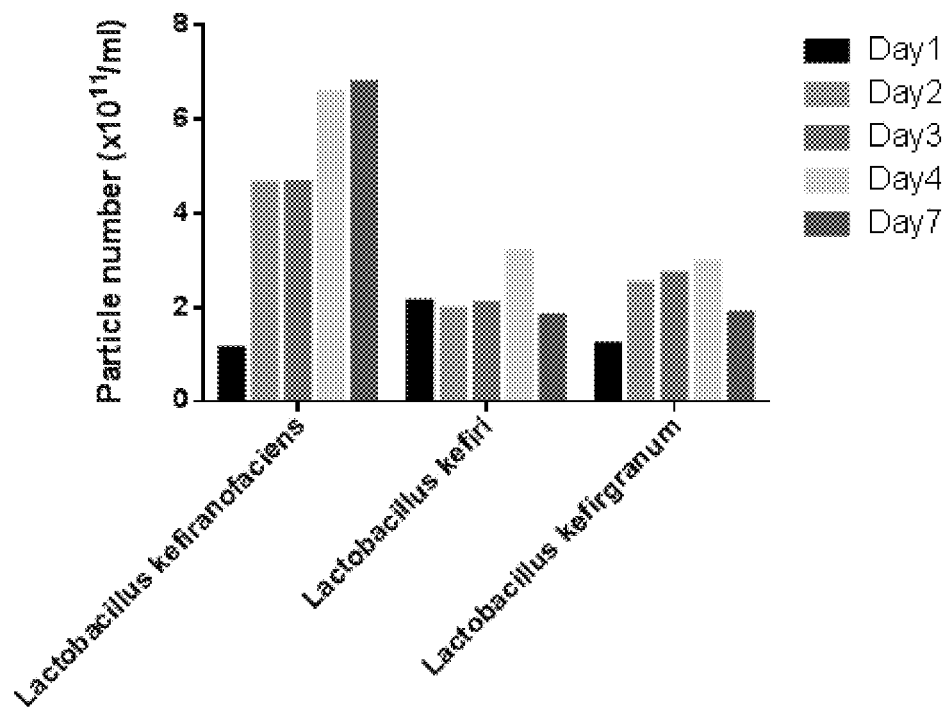
FIG. 2 shows the results by measuring the respective numbers of particles in the *Lactobacillus kefiri*-derived, *Lactobacillus kefiranofaciens*-derived, and *Lactobacillus kefirgranum*-derived extracellular vesicles with a nanoparticle tracking analyzer, according to the culturing times thereof.

The obtained pellets were respectively suspended in phosphate buffered saline (1 ml) and then the numbers of the respective extracellular vesicles were measured using a nanoparticle tracking analyzer (Nanosight NS300). The results thereof are shown in FIG. 2. As shown in FIG. 2 (*a*) and (*b*), said three microorganisms showed similar changes in the numbers of particles in the respective extracellular vesicles, according to the culturing times. Especially, it has been confirmed that all the three microorganisms show the highest numbers of particles in the culture on the fourth day of the suspension culture.

Example 3: Yields of the Kefir Grains-Derived Extracellular Vesicles According to the Methods for Preparing the Same The extracellular vesicles were prepared, according to the following three methods, from the cultures on the fourth day of the suspension cultures of *Lactobacillus* kefiranofaciens, *Lactobacillus kefiri* and *Lactobacillus kefirgranum*.

1. Preparation of the Extracellular Vesicles Using Ultracentrifugation (Ultracentrifugation Method)

Each culture was centrifuged under the rotation speed of 300 g at 4° C. for 10 minutes. Each resulting supernatant was centrifuged under the rotation speed of 1,200 g at 4° C. for 20 minutes. Each resulting supernatant was centrifuged under the rotation speed of 10,000 g at 4° C. for 30 minutes. Each resulting supernatant was ultra-centrifuged under the rotation speed of 110,000 g at 4° C. for 1 hour and 10 minutes to discard the resulting supernatant, thereby obtaining the respective pellets.

2. Preparation of the Extracellular Vesicles Using ExoQuick™ Exosome Precipitation Solution (Exoquick Method)

Each culture was centrifuged under the rotation speed of 3,000 g at 4° C. for 15 minutes. To each resulting supernatant, was added the ExoQuick™ Exosome Precipitation Solution in a ratio of 2 ml per 10 ml of the supernatant. After incubating at 4° C. overnight, each mixture was centrifuged under the rotation speed of 1,500 g at 4° C. for 30 minutes to discard the supernatant; thereby obtaining the respective pellets.

3. Preparation of the Extracellular Vesicles According to a Precipitation Method (Precipitation Method)

Each culture was centrifuged under the rotation speed of 5,000 g at 4° C. for 10 minutes. To each resulting supernatant, was added 1N sodium acetate in a ratio of 1 ml per 10 ml of the supernatant. After incubating in an ice bath for 45 minutes, each mixture was centrifuged under the rotation speed of 5,000 g at 4° C. for 10 minutes to discard the supernatant. Each resulting precipitate was washed with 0.1N sodium acetate; and then centrifuged under the rotation speed of 5,000 g at 4° C. for 10 minutes to discard the supernatant, thereby obtaining the respective pellets.

Figure 3:
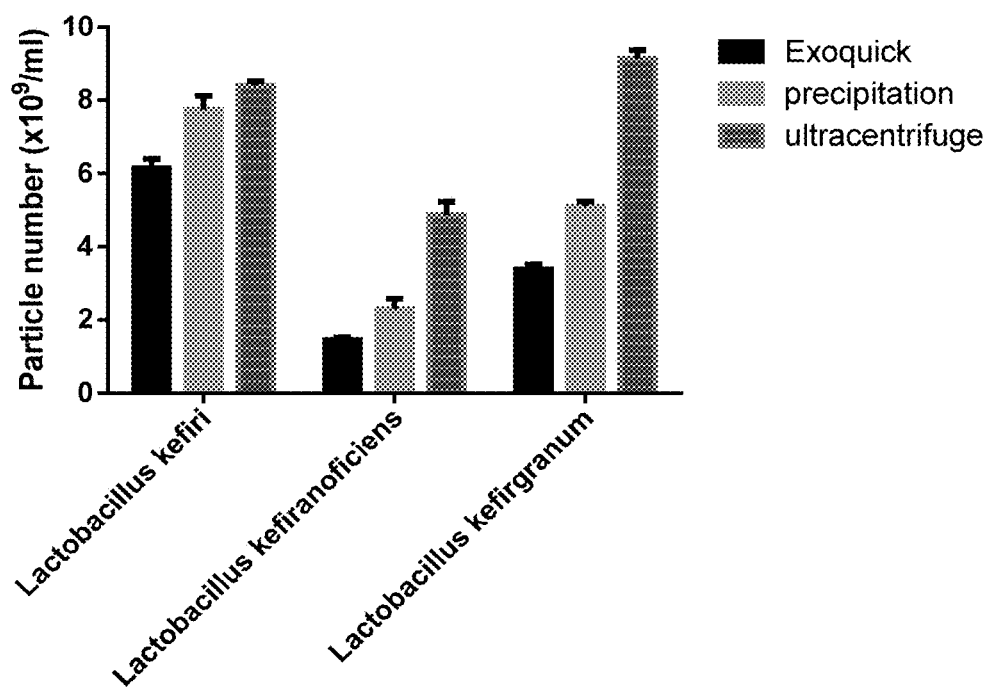
FIG. 3 shows the results by measuring the respective numbers of particles in the *Lactobacillus kefiri*-derived, *Lactobacillus kefiranofaciens*-derived, and *Lactobacillus kefirgranum*-derived extracellular vesicles with a nanoparticle tracking analyzer, according to the methods for preparing the same.

The respective pellets obtained according to the above three methods were suspended in phosphate buffered saline (1 ml) and then the numbers of the respective extracellular vesicles therein were measured using a nanoparticle tracking analyzer (Nanosight NS300). The results thereof are shown in FIG. 3. As shown in FIG. 3, it can be confirmed that the method using ultracentrifugation provided the extracellular vesicles in highest yield.

Example 4: Preparations of the Kefir Grains-Derived Extracellular Vesicles

The mixed microorganisms of *Lactobacillus kefiranofaciens* (KCTC 5075, Korean Collection for Type Cultures), *Lactobacillus kefiri* (KCTC 3611, Korean Collection for Type Cultures) and *Lactobacillus kefirgranum* (KCTC 5086, Korean Collection for Type Cultures) (in substantially the same cell numbers) were cultured in the same procedures as in Example 1. The extracellular vesicles were obtained from the culture, according to the ultracentrifugation method of Example 3.

Experimental Example 1: Evaluation of Anti-Inflammatory Effects of the Kefir Grains-Derived Extracellular Vesicles (1)

The human colon cancer cell line CaCo-2 (Korea cell line bank. KCLB), in which inflammation had been induced with TNF-α (20 ng/ml), was added to each well of a 12-well plate ($1 \times 10^6$ cells per well), along with Eagle's minimum essential medium (MEM) containing 100 units/mL of penicillin, 100 μg/mL of streptomycin, and 10% fetal bovine serum. The respective extracellular vesicles obtained in Example 1 in phosphate buffered saline were added thereto in the amounts of $1 \times 10^3$, $1 \times 10^6$, and $1 \times 10^9$ particles per well, followed by incubating for 24 hours. RNAs were extracted from the cells of each group. The complementary cDNAs were synthesized using an intron premix and then the real-time PCRs (RT-PCRs) were carried out to measure the expressions of the proinflammatory cytokines, IL-8 and TNF-α. The results thereof are shown in FIG. 4.

Figure 4:
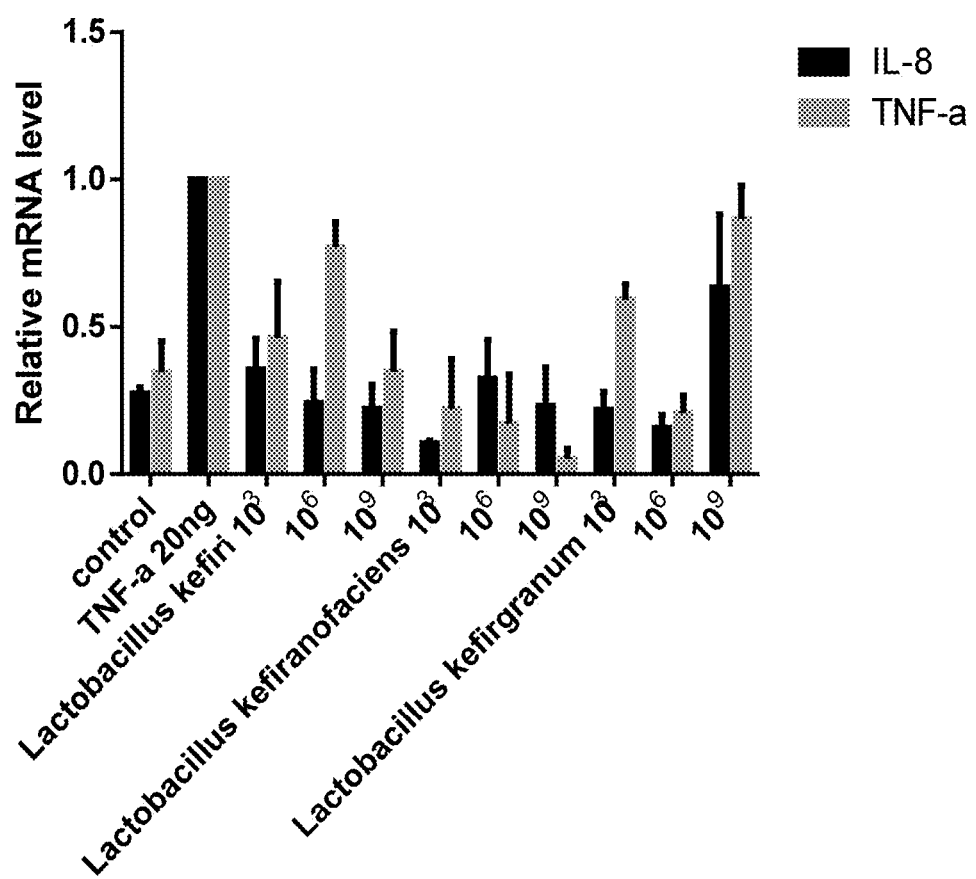
FIG. 4 shows the results by measuring the mRNA expression levels of the proinflammatory cytokines, IL-8 and TNF-α, after treating the inflammation-induced human colon cancer cell line CaCo-2 with the extracellular vesicles of the present invention.

As shown in FIG. 4, the treatments of the extracellular vesicles according to the present invention showed significant reduction in the expression levels of IL-8 and TNF-α. Especially, it can be confirmed that the extracellular vesicles derived from *Lactobacillus kefiranofaciens* showed excellent anti-inflammatory effects.

Experimental Example 2: Evaluation of Anti-Inflammatory Effects of the Kefir Grains-Derived Extracellular Vesicles (2)

Figure 5:
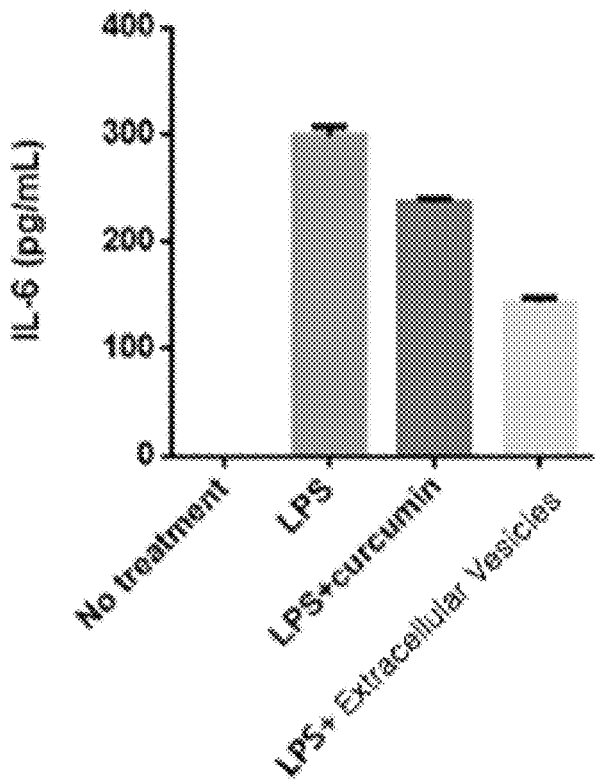
FIG. 5 shows the results by measuring the expression level of IL-6, when the mouse macrophage cell line (Raw246.7 cells) was treated with the extracellular vesicles of the present invention, followed by treating with LPS.
Figure 6:
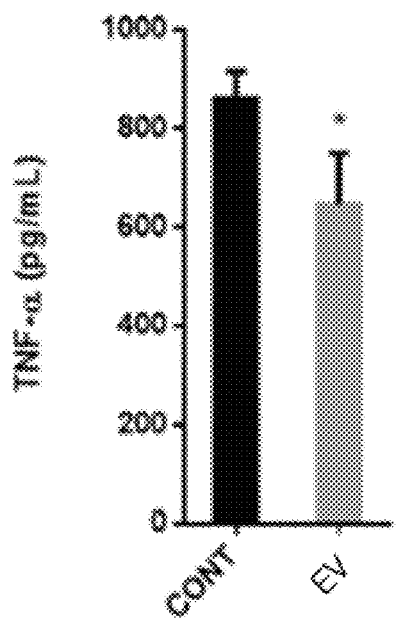
FIG. 6 shows the results by measuring the expression level of TNF-α, when the mouse macrophage cell line (Raw246.7 cells) was treated with the extracellular vesicles of the present invention, followed by treating with LPS.

The mouse macrophage cell line Raw246.7 was cultured in a DMEM medium supplemented with 10% FBS and 1% penicillin-streptomycin for 48 hours and then treated with the extracellular vesicles obtained in Example 4 in the amount of $1 \times 10^9$ particles/ml. The cells were cultured for 24 hours and then treated with LPS (100 ng/ml) for 6 hours. The expression levels of IL-6 and TNF-α were measured using RT-PCR and ELISA. The results thereof are shown in FIGS. 5 and 6. As a positive control group, the cells were treated with curcumin (10 μM).

As shown in FIGS. 5 and 6, the treatment of the extracellular vesicles according to the present invention showed significant reduction by more than half in the expression levels of IL-6 and TNF-α, in comparison with the non-treated group or curcumin-treated group.

Experimental Example 3: Evaluation of Anti-Inflammatory Effects of the Kefir Grains-Derived Extracellular Vesicles (3)

Caco-2 cells were cultured in a MEM supplemented with 10% FBS, 100 units/mL penicillin, 100 μg/mL streptomycin, 0.1 mmol/l non-essential amino acids, and 1 mmol/l sodium pyruvate, in a 37° C. incubator of 5% $CO_2$ and 95% air. When the cells were about 80% confluent, the cells were detached with 0.25% trypsin and then inoculated on each well of a 24-well plate ($2 \times 10^4$ cells per well), along with Eagle's minimum essential medium (MEM) containing 100 units/mL of penicillin, 100 μg/mL of streptomycin, and 10% fetal bovine serum. Each well was treated with TNF-α (20 ng/ml) for 6 hours and then treated with the extracellular vesicles obtained in Example 4 in the amount of $1 \times 10^9$ particles/ml. After the cells were cultured for 24 hours, the expression levels of IL-8 and TNF-α and the secretion level of IL-8 in comparison with the control group were measured using RT-PCR and ELISA. The results thereof are shown in FIGS. 7 to 9.

Figure 7:
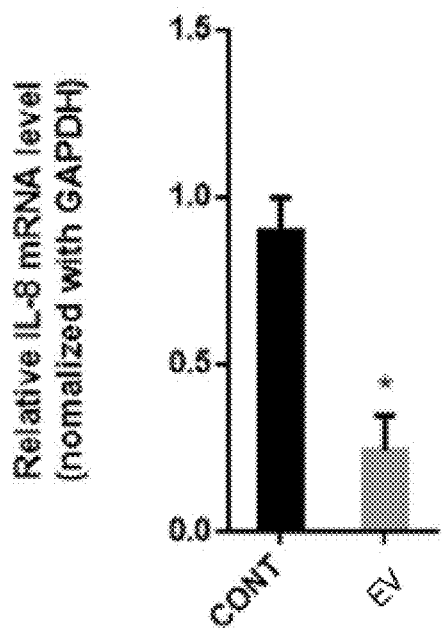
FIG. 7 shows the results by measuring the expression level of IL-8, when Caco-2 cells were treated with TNF-α, followed by treating with the extracellular vesicles of the present invention.
Figure 8:
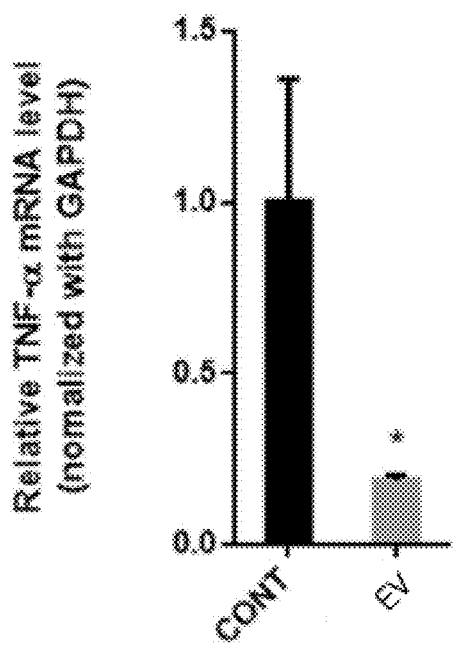
FIG. 8 shows the results by measuring the expression level of TNF-α, when Caco-2 cells were treated with TNF-α, followed by treating with the extracellular vesicles of the present invention.
Figure 9:
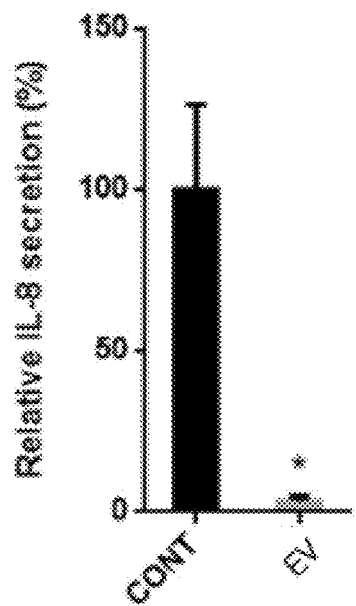
FIG. 9 shows the results by measuring the secretion level of IL-8 in comparison with the control group, when Caco-2 cells were treated with TNF-α, followed by treating with the extracellular vesicles of the present invention.

As shown in FIGS. 7 to 9, the treatment of the extracellular vesicles according to the present invention showed significant reduction in the mRNA expression levels of IL-8 and TNF-α, as well as in the secretion level of IL-8.

Experimental Example 4: Evaluation of Inhibitory Effects of the Kefir Grains-Derived Extracellular Vesicles Against Colitis Colitis mouse models were prepared by inducing colitis in BALB/c mice with 2,4,6-trinitrobenzenesulfonic acid (TNBS). Specifically, BALB/c mice were anesthetized with ether and then 0.1 ml of a solution of TNBS (2.5 g) in 50% ethanol (0.1 ml) was injected into the colon lumen through the anus, using a 1 ml syringe with a round end. The mice were held vertically for 30 seconds to induce colitis. The extracellular vesicles obtained in Example 4 were suspended in phosphate buffered saline (0.1 ml) and then orally administered at a dose of 10 μg/mouse or 1 mg/mouse once a day for 3 days from the next day. In case of the normal control group, 0.1 ml of physiological saline was orally administered. As a positive control group, prednisolone, an anticolitis agent, was orally administered in the amount of 2 mg/kg. On the next day after the completion of the administrations, the mice were euthanized using the carbon dioxide inhalation and then the colon from cecum to the site just before the anus was extracted.

(1) Histological Evaluation

Figure 10:
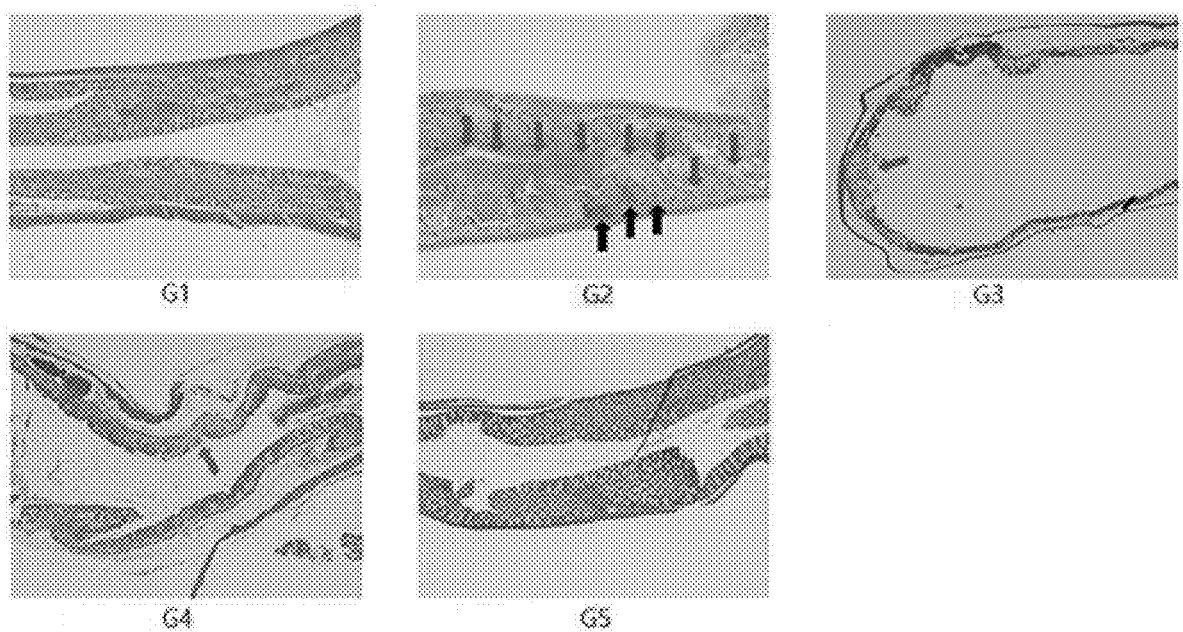
FIG. 10 shows the cross-sectional photographs of the colon tissues obtained by treating the TNBS-induced colitis mouse models with the extracellular vesicles of the present invention.
Figure 11:
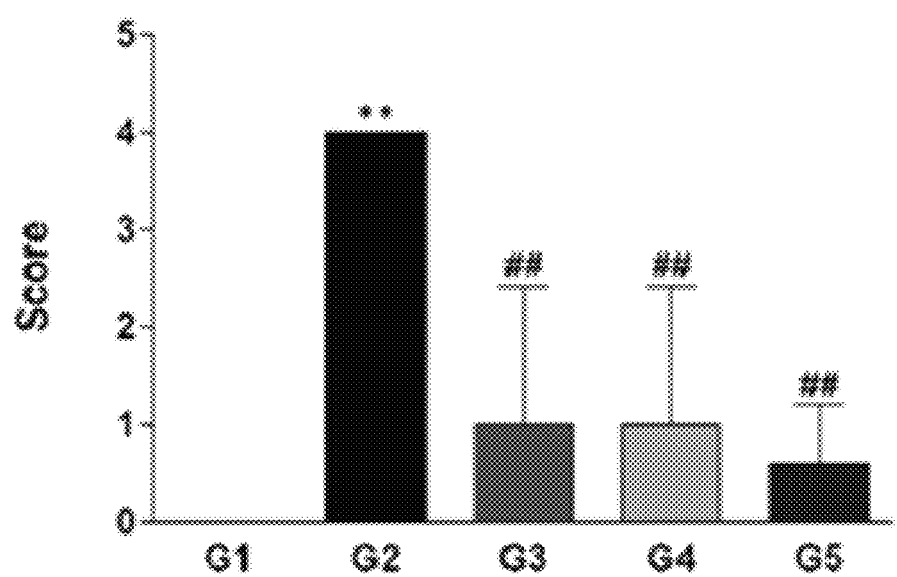
FIG. 11 shows the histological evaluation results of the colon tissues obtained by treating the TNBS-induced colitis mouse models with the extracellular vesicles of the present invention.
Figure 12:
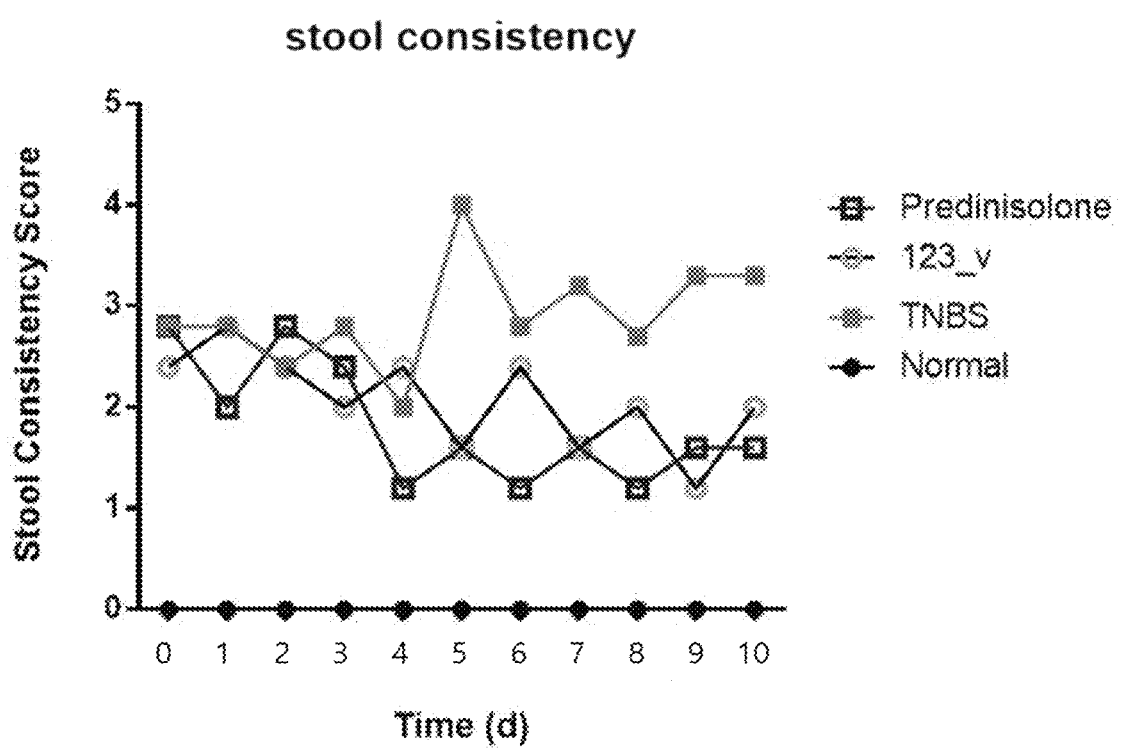
FIG. 12 shows the results by evaluating the stool consistency, when the TNBS-induced colitis mouse models were treated with the mixed microorganism-derived extracellular vesicles (123_v) according to the present invention.
Figure 13:
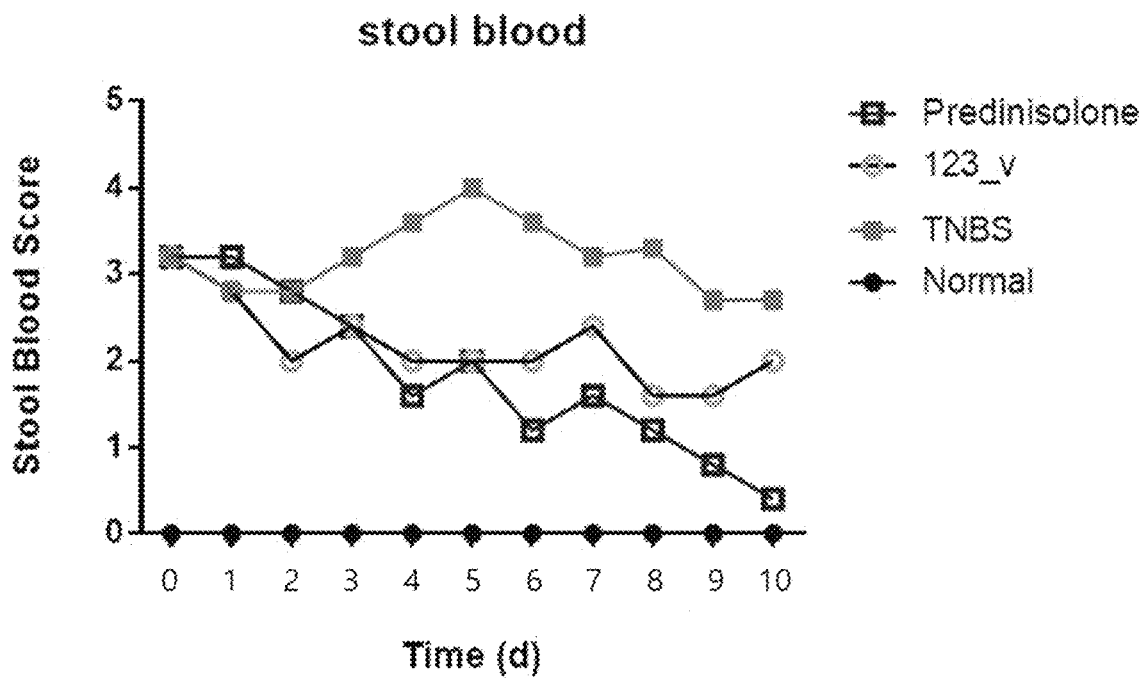
FIG. 13 shows the results by evaluating the stool bleeding, when the TNBS-induced colitis mouse models were treated with the mixed microorganism-derived extracellular vesicles (123_v) according to the present invention.
Figure 14:
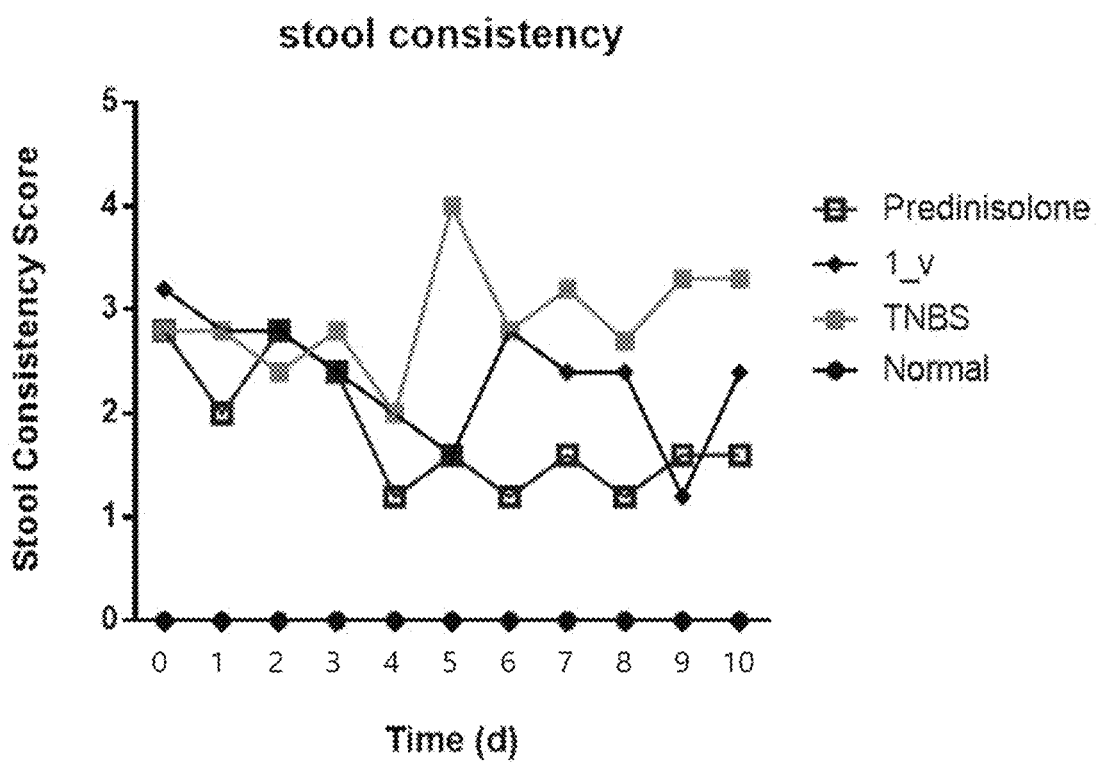
FIG. 14 shows the results by evaluating the stool consistency, when the TNBS-induced colitis mouse models were treated with the *Lactobacillus kefirgranum*-derived extracellular vesicles (1_v) according to the present invention.
Figure 15:
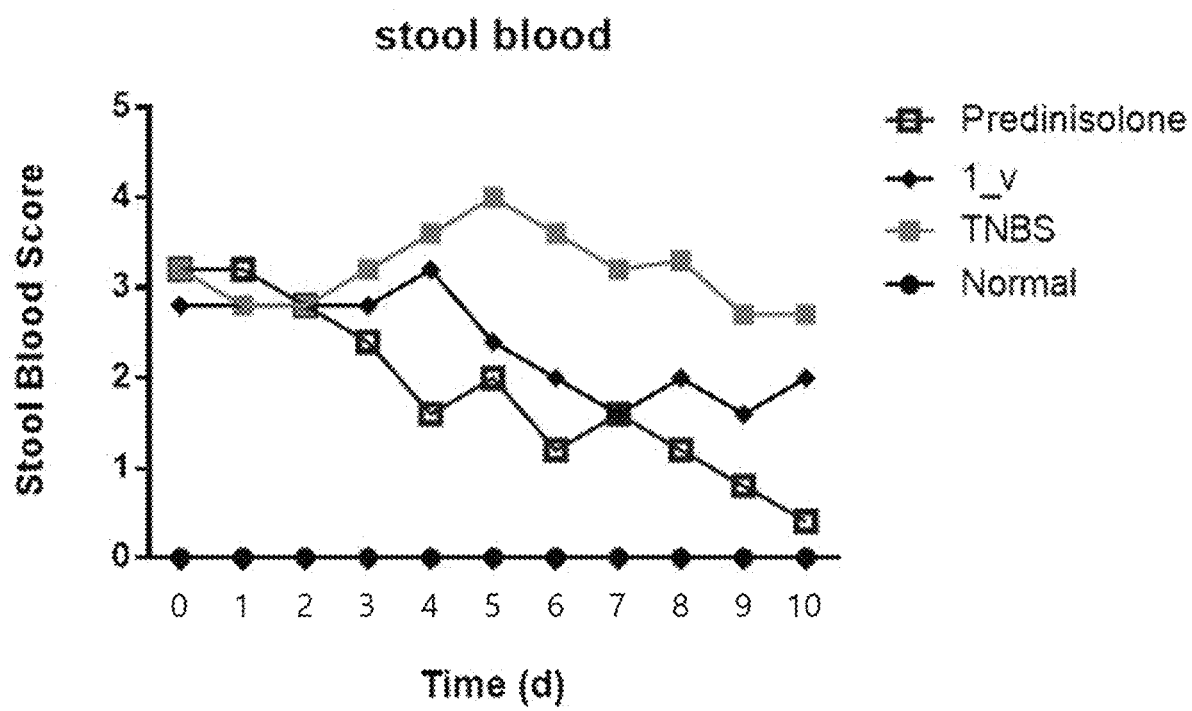
FIG. 15 shows the results by evaluating the stool bleeding, when the TNBS-induced colitis mouse models were treated with the *Lactobacillus kefirgranum*-derived extracellular vesicles (1_v) according to the present invention.

The extracted colon tissues were stained with hematoxylin and eosin (H&E). The cross-sectional photographs are shown in FIG. 10. The length and histology of the colon of each group were observed and scored according to criteria of the following table 2 (Hollenbach et al., 2005 criteria for colitis). The results thereof are shown in FIG. 11.

TABLE 2

| Macroscopic Score | Criteria |
| --- | --- |
| 0 | No ulceration nor inflammation found |
| 1 | Non-hemorrhagic congestion found |
| 2 | Congestive ulceration found |
| 3 | Ulceration and inflammation found only in one site |
| 4 | Ulceration and inflammation found in two or more sites |
| 5 | Ulcer enlarged to 2 cm or more |

As shown in FIG. 10, severe epithelial necrosis, hemorrhage, infiltration of inflammatory cells, edema and ulceration were observed in the colon of the colitis mouse model. However, when the extracellular vesicles according to the present invention were administered to the colitis mouse model, the histological damages were significantly alleviated in a concentration-dependent manner. In addition, as shown in FIG. 11, when the extracellular vesicles according to the present invention were administered to the colitis mouse model, colonic bleeding was also decreased in a concentration-dependent manner. These effects were superior to the positive control group in which prednisolone was administered in a large amount (i.e., 2 mg/kg).

(2) DAI Evaluation

It has been known that a disease activity index (DAI) score can be accessed to evaluate the severity of acute colitis induced by TNBS. While the extracellular vesicles according to the present invention were being administered, the concentration and color of the stools were observed at the same time every day. The stool consistency and the stool bleeding were measured and the results thereof are shown in FIGS. 12 to 15. The evaluation criteria of DAI are shown in following table 3. In the DAI evaluations, the extracellular vesicles (1_v) derived from *Lactobacillus kefirgranum* (obtained by the ultracentrifugation method in Example 3) were also administered in the same procedures as in the above, in addition to the extracellular vesicles (123_v) derived from the mixed to microorganisms (obtained in Example 4).

TABLE 3

| Stool consistency | | Stool bleeding | |
| --- | --- | --- | --- |
| 0 | Formed | 0 | Normal color |
| 2 | Loose stool | 2 | Fecal occult blood test positive |
| 4 | Diarrhea | 4 | Gross bleeding |

As shown in FIGS. 12 to 15, when the extracellular vesicles (123_v) derived from the mixed microorganisms and the extracellular vesicles (1_v) derived from *Lactobacillus kefirgranum* were administered to the colitis mouse model, the DAI scores thereof were lowered to the level equal to those of the prednisolone-administered positive control group. Therefore, it can be confirmed that the administration of the extracellular vesicles according to the present invention can improve bowel movement significantly.

(3) Evaluation of MPO Activity

Myeloperoxidase (MPO) activities, one of the biomarkers of inflammation, were measured in the extracted colon tissues, using the MPO ELISA kit (Hycult Biotech, HK105). For the MPO assay, the colon tissues were homogenously pulverized with a homogenizer and then centrifuged for 15 minutes. The resulting supernatant (100 μL) and the standard solution (100 μL) were added to each well coated with the antibody. The well plate was sealed with a cover to prevent air from entering the well, followed by reacting at room temperature for 1 hour. Each well was washed four times with the washing buffer. At that time, the washing buffer was completely removed. After the tracer solution (100 μL) was added to each well, the cover was attached, followed by reacting at room temperature for 1 hour. Each well was washed four times in the same manner. After a diluted streptavidin-peroxidase solution (100 μL) was added to each well, the cover was attached, followed by reacting at room temperature for 1 hour. Each well was washed four times and the TMB substrate (100 μL) was added to each well. After reacting for 30 minutes under light shielding, the stop solution (100 μL) was added to each well. The absorbance was measured at 450 nm and the MPO activities of the test samples were determined using a standard curve prepared with the standard solution. The results thereof are shown in FIG. 16.

Figure 16:
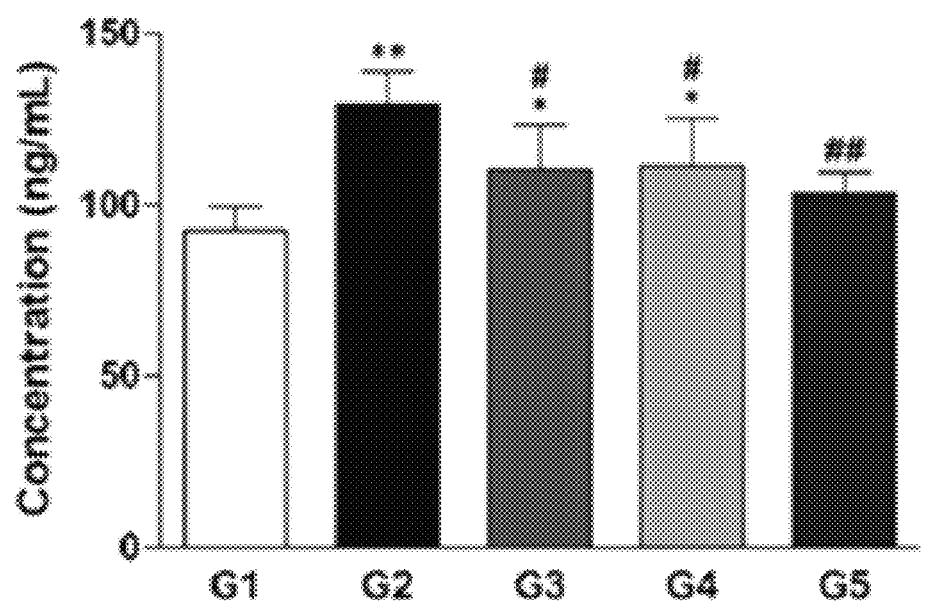
FIG. 16 shows the results by measuring the changes in MPO activity, when the TNBS-induced colitis mouse models were treated with the extracellular vesicles according to the present invention.

As shown in FIG. 16, when the extracellular vesicles according to the present invention were administered to the colitis mouse model, the MPO activities thereof were lowered to the level equal to that of the prednisolone-administered positive control group.

Experimental Example 5: Evaluation of Inhibitory Effects of the Kefir Grains-Derived Extracellular Vesicles Against Irritable Bowel Syndrome IBS mouse models were prepared by inducing irritable bowel syndrome in BALB/c mice with acetic acid. Specifically, BALB/c mice were anesthetized with ether and then 0.1 ml of 5% acetic acid was injected into the colon lumen through the anus, using a 1 ml syringe with a round end. The mice were held vertically for 30 seconds to induce irritable bowel syndrome. The extracellular vesicles obtained in Example 4 were suspended in phosphate buffered saline (0.1 ml) and then orally administered at a dose of 10 μg/mouse once a day for 3 days from the next day (Group A5). In case of the IBD-induced control group (Group A2), 0.1 ml of physiological saline was orally administered. For comparison, prednisolone (2 mg/kg) (Group A3)/the mixed microorganisms (5×10$^7$ CFU) of *Lactobacillus kefiranofaciens* (KCTC 5075, Korean Collection for Type Cultures), *Lactobacillus kefiri* (KCTC 3611, Korean Collection for Type Cultures) and *Lactobacillus kefirgranum* (KCTC 5086, Korean Collection for Type Cultures) (Group A4)/the commercially available *Lactobacillus* strains (5×10$^7$ CFU) (Group A6)/and the commercially available *Lactobacillus* strains (5×10$^7$ CFU)+the extracellular vesicles obtained in Example 4 (10 μg/mouse, suspended in PBS) (Group A7) were also orally administered. During the administrations, the stool color of each group was observed at the same time every day. The stool bleeding of each group was measured according to the evaluation criteria of the above table 3 and the results thereof are shown in FIG. 17.

Figure 17:
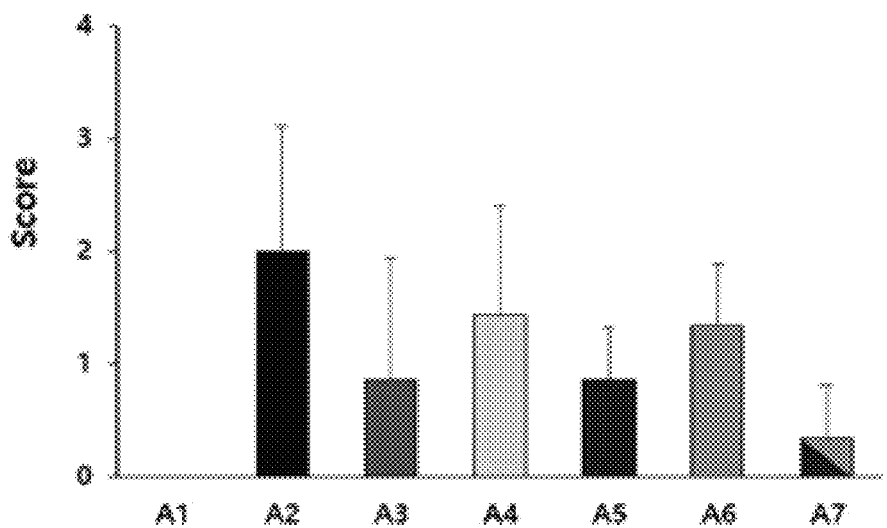
FIG. 17 shows the results by evaluating the stool bleeding, when the acetic acid-induced IBS mouse models were treated with the extracellular vesicles according to the present invention.

As shown in FIG. 17, when the extracellular vesicles according to the present invention were administered to the IBS mouse model, the colonic bleeding thereof was significantly lowered, in comparison with those of the groups administered with the mixed microorganisms per se and with the commercially available *Lactobacillus* strains. And also, it can be confirmed that, when the extracellular vesicles according to the present invention were administered along with the commercially available *Lactobacillus* strains, the colonic bleeding thereof was more significantly lowered.

Figure 18:
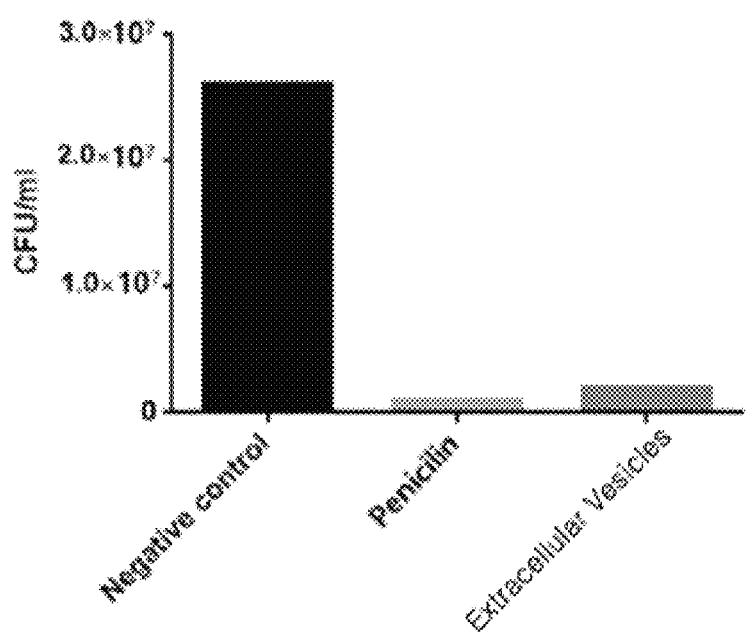
FIG. 18 shows the results by measuring the number of viable cells, when *Staphylococcus epidermidis* strains were treated with the extracellular vesicles according to the present invention.

Experimental Example 6: Evaluation of Antimicrobial Effects of the Kefir Grains-Derived Extracellular Vesicles We evaluated antimicrobial effects of the extracellular vesicles according to the present invention against harmful enteric bacteria. *Staphylococcus epidermidis*, one of the harmful enteric bacteria, was cultivated in a liquid nutrient medium for 24 hours and then treated with 500 μg/ml of the extracellular vesicles obtained in Example 4. After culturing at 37° C. for 3 hours additionally, the number of viable cells was counted and the results thereof are shown in FIG. 18. The negative control group was treated with distilled water and the positive control group was treated with penicillin (10 μg/ml).

As shown in FIG. 18, it can be confirmed that the treatment of the extracellular vesicles according to the present invention inhibited the proliferation of *Staphylococcus epidermidis*, thereby inducing the death thereof, in the similar level as in the treatment of penicillin as a positive control.

Figure 19A:
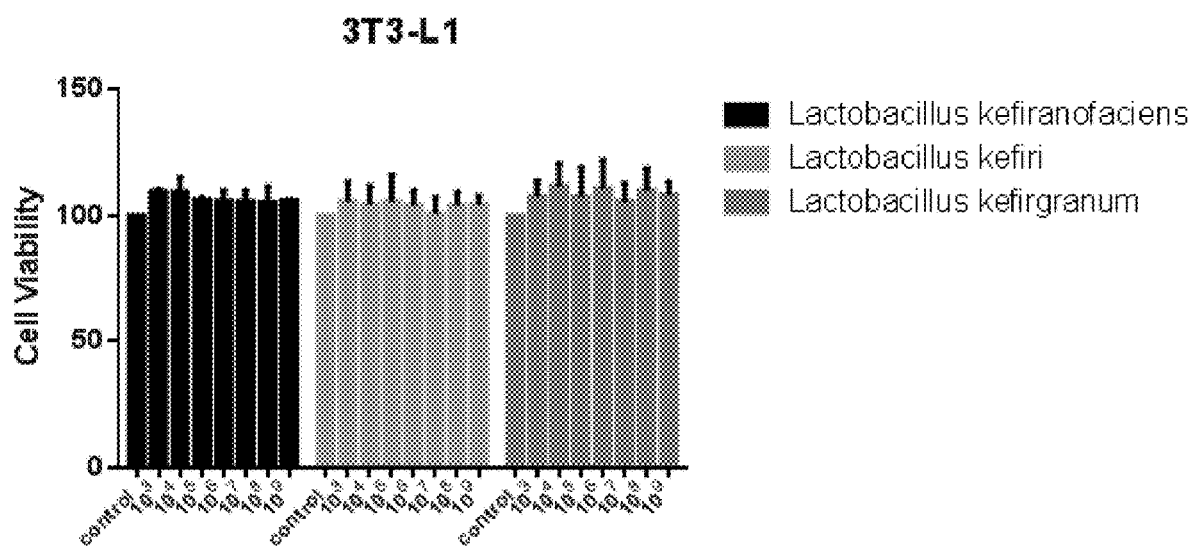
FIG. 19a shows the results by measuring the cell viability, when 3T3-L1 cells were treated with the extracellular vesicles according to the present invention.
Figure 19B:
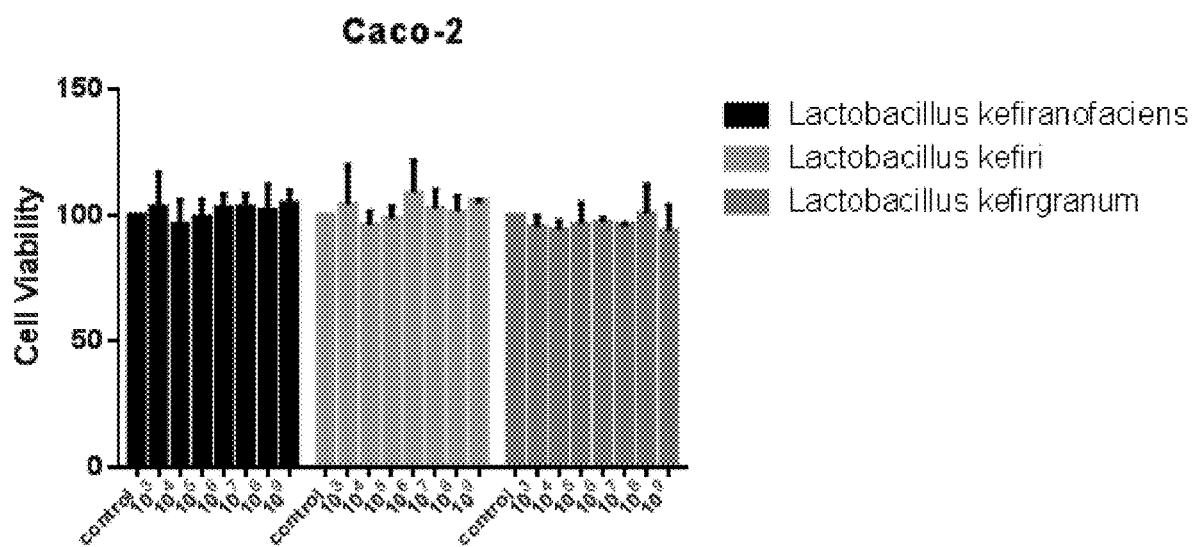
FIG. 19b shows the results by measuring the cell viability, when CaCo-2 cells were treated with the extracellular vesicles according to the present invention.

Experimental Example 7: Evaluation of Safety of the Kefir Grains-Derived Extracellular Vesicles We performed the safety evaluation of the extracellular vesicles according to the present invention. 3T3-L1 cells (Korea cell line bank, KCLB) and CaCo-2 cells (Korea cell line bank, KCLB) were treated with the extracellular vesicles obtained by the ultracentrifugation method in Example 3 in the amounts of 1×10$^3$ to 1×10$^9$ particles. The MTS reagent (Promega, USA) was diluted with the basal medium (FBS free, 1% p/s) at the ratio of 1:5 and the diluted solution was added to each well in the amount of 500 μL per well. After reacting for 1 hour and 30 minutes, the absorbance was measured at a wavelength of 490 nm to evaluate the changes in cell viability. The results thereof are shown in FIGS. 19a and 19b. No treatment was performed for the control group.

As shown in FIGS. 19a and 19b, it can be confirmed that there was observed no cytotoxicity, even when the extracellular vesicles according to the present invention were treated up to 1×10$^9$ particles.

Figure 20:
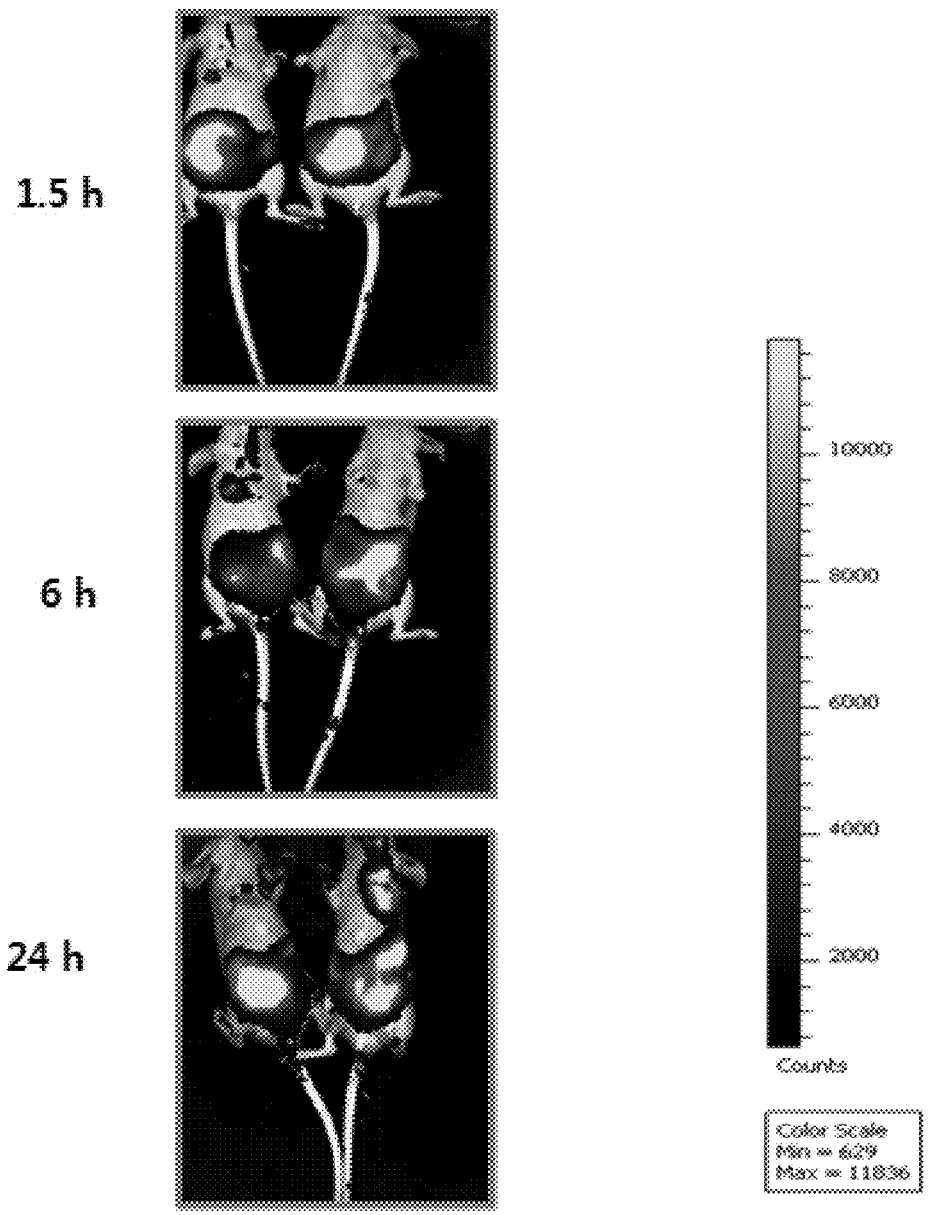
FIG. 20 shows the results by measuring the biodistribution, when the Kefir grains-derived extracellular vesicles according to the present invention were orally administered to mice.

Experimental Example 8: Biodistribution of the Kefir Grains-Derived Extracellular Vesicles The extracellular vesicles (EVs) obtained in Example 4 were incubated with 1 μL of 10 mM Flamma® 675 for 2 hours in dark. The EVs were washed with 10 mL of PBS and subjected to ultracentrifugation under the rotation speed of 110,000 g at 4° C. for 1 hour and 10 minutes, thereby obtaining fluorescently labeled EVs. The resulting EVs (1×10$^9$ particles) were orally administered to mice. Migration of fluorescently labeled EVs in mouse organs was detected using an IVIS systems (Perkin Elmer, Waltham, Mass.). During the procedure, the mice were anesthetized using Zoletil 50 (Virbac, 5 mg/kg) and xylazine (Rompun, Bayer AG, Germany, 2.5 mg/kg). The representative results thereof are shown in FIG. 20. As shown in FIG. 20, it can be confirmed that the orally administered extracellular vesicles maintain the distribution in the gastrointestinal tract for significantly extended period (e.g., for 24 hours more).

Experimental Example 9: Comparison of the Efficacies of the Mixed Microorganisms and the Kefir Grains-Derived Extracellular Vesicles in the DSS-Induced Colitis Mouse Models Colitis mouse models were prepared by inducing colitis in C57BL/6 mice with dextran sulfate sodium salt (DSS). Specifically, the administration of DSS (Sigma-Aldrich) (3% (w/v) in drinking water ad libitum) in C57BL/6 mice induced colitis in 6 days. The mice were randomly divided to 5 groups as follows:

G1: Distilled water was administered by intragastric injection (IG) once a day for 13 days.

G2: Distilled water was administered by intragastric injection (IG) once a day for 13 days and DSS was supplied in mouse drinking water from 7th to 13th day.

G3: Prednisolone (2 mg/kg) was also administered by intragastric injection (IG) once a day for 13 days and DSS was supplied in mouse drinking water from 7th to 13th day.

G4: The mixed microorganisms (1×10$^9$ CFU) of *Lactobacillus kefiranofaciens* (KCTC 5075, Korean Collection for Type Cultures), *Lactobacillus kefiri* (KCTC 3611, Korean Collection for Type Cultures) and *Lactobacillus kefirgranum* (KCTC 5086, Korean Collection for Type Cultures) were administered by intragastric injection (IG) once a day for 13 days and DSS was supplied in mouse drinking water from 7th to 13th day.

G5: The extracellular vesicles obtained in Example 4 (1×10$^9$ particles) were administered by intragastric injection (IG) once a day for 13 days and DSS was supplied in mouse drinking water from 7th to 13th day.

Figure 21:
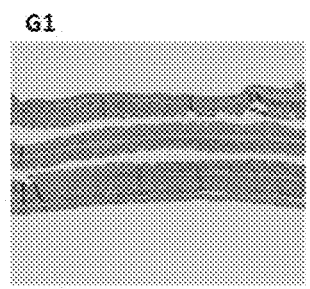
FIG. 21 shows the results by comparing the efficacies of the mixed microorganisms and the Kefir grains-derived extracellular vesicles according to the present invention in the DSS-induced colitis mouse models.
Figure 21:
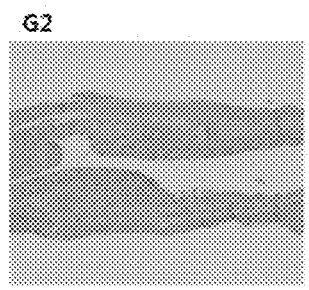
Figure 21:
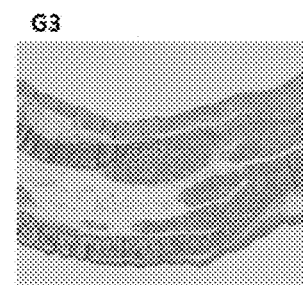
Figure 21:
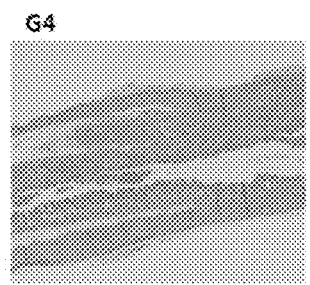
Figure 21:
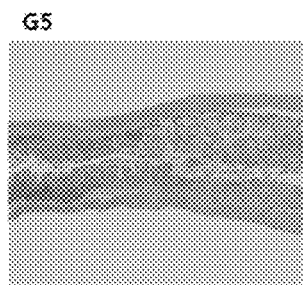
Figure 21:
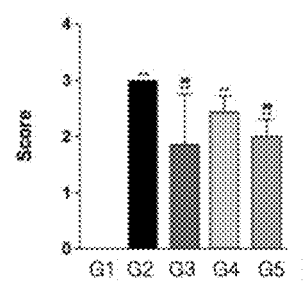

The histological evaluations of each group were performed according to the same manners and criteria as in (1) of Experimental Example 4. The results thereof are shown in FIG. 21. As shown in FIG. 21, the histological damages in Group 5 were alleviated more significantly, in comparison with those of Group 4.

The invention claimed is:

1. A method for ameliorating or treating inflammatory bowel disease and/or irritable bowel syndrome in a mammal in need thereof, comprising administering to the mammal a therapeutically effective amount of an isolated extracellular vesicles derived from one or more Kefir grains selected from the group consisting of *Lactobacillus kefiranofaciens*, *Lactobacillus kefiri*, and *Lactobacillus kefirgranum*, wherein the isolated extracellular vesicles are in the form of exosomes having a diameter ranging from 30 to 300 nm, thereby ameliorating or treating inflammatory bowel disease and/or irritable bowel syndrome in said mammal in need thereof.

2. The method according to claim 1, wherein the inflammatory bowel disease is Crohn's disease or colitis.

3. The method according to claim 1, wherein the exosomes have a mean diameter ranging from 120 to 190 nm.

4. The method according to claim 1, wherein the extracellular vesicles are prepared by a process comprising (a) culturing one or more Kefir grains in a medium; (b) performing a centrifugation of the culture obtained in Step (a) to obtain a supernatant, thereby removing the Kefir grains; and (c) performing an ultracentrifugation of the supernatant obtained in Step (b) to obtain the resulting extracellular vesicles in the form of pellets.

5. The method according to claim 4, wherein the centrifugation of Step (b) is carried out under a rotation speed ranging from 5,000 g to 20,000 g and at a temperature below 20° C.

6. The method according to claim 4, wherein the centrifugation of Step (b) is carried out by (i) a first centrifugation of the culture obtained in Step (a) under a rotation speed ranging from 100 g to 1,000 g and at a temperature below 20° C. to obtain a supernatant; (ii) a second centrifugation of the supernatant obtained in Step (i) under a rotation speed ranging from 1,000 g to 5,000 g and at a temperature below 20° C. to obtain a supernatant; and then (iii) a third centrifugation of the supernatant obtained in Step (ii) under a rotation speed ranging from 5,000 g to 20,000 g and at a temperature below 20° C.

7. The method according to claim 4, wherein the ultracentrifugation of Step (c) is carried out under a rotation speed ranging from 100,000 g to 150,000 g and at a temperature below 20° C.

* * * * *